United States Patent [19]

Schoellkopf et al.

[11] 4,280,008

[45] Jul. 21, 1981

[54] CHIRALLY SUBSTITUTED 2-IMIDAZOLIN-5-ONES

[75] Inventors: Ulrich Schoellkopf, Bovenden; Hans-Heinrich Hausberg, Goettingen; Walter Boell, Dannstadt-Schauernheim; Hans-Joachim May, Neustadt; Horst Koenig, Ludwigshafen, all of Fed. Rep. of Germany

[73] Assignee: BASF Aktiengesellschaft, Fed. Rep. of Germany

[21] Appl. No.: 861,731

[22] Filed: Dec. 16, 1977

[30] Foreign Application Priority Data

Dec. 24, 1976 [DE] Fed. Rep. of Germany ....... 2658941

Dec. 24, 1976 [DE] Fed. Rep. of Germany ....... 2658942

[51] Int. Cl.$^2$ .......... C07D 233/32

[52] U.S. Cl. .......... 548/301; 546/211

[58] Field of Search .......... 548/301

[56] References Cited

U.S. PATENT DOCUMENTS

| | | | |
|---|---|---|---|
| 3,428,646 | 2/1969 | Hellerbach | 548/301 |
| 3,894,008 | 7/1975 | Irvine | 548/301 |

OTHER PUBLICATIONS

Asker et al., Chem. Abst. 1972, vol. 76, No. 59522u.

Iida, Chem. Abst. 1962, vol. 58, No. 4539c.

*Primary Examiner*—Alan L. Rotman

*Assistant Examiner*—Natalia Harkaway

*Attorney, Agent, or Firm*—Keil & Witherspoon

[57] ABSTRACT

Chirally substituted 2-imidazolin-5-ones and their use as intermediates for the preparation of optically active aminoacids, especially of optically active α-substituted aminoacids.

4 Claims, No Drawings

CHIRALLY SUBSTITUTED 2-IMIDAZOLIN-5-ONES

The present invention relates to chirally substituted 2-imidazolin-5-ones and their use as intermediates for the preparation of optically active aminoacids, especially of optically active α-substituted aminoacids.

An optically active compound is as a rule prepared from the racemic compound which is obtained when the asymmetric molecule is synthesized from symmetrical components. The resolution of a racemate into the optically active components is as a rule achieved in either of two ways, namely by spontaneous resolving crystallization or by utilizing an optically active auxiliary.

Both methods have been described for, for example, the synthesis of optically active aminoacids, e.g. α-methyl-DOPA. Resolution by crystallization can be carried out at the stage of the aminoacid or at an intermediate stage; resolution by means of an auxiliary compound, e.g. an optically active amine or an acid, is normally carried out at an intermediate stage (German Published Application DAS No. 1,593,989).

The unmistakable disadvantage of these processes is that at most half the racemate employed can be obtained in the form of the desired enantiomer, whilst the second half, which is accounted for by the undesired enantiomer, is either lost or must be racemized by an involved method, so that it can be re-used in the resolution stage. This also applies for biochemical methods of resolving racemates, in which, in many cases, one of the enantiomers, namely the one which is not required, is destroyed by degradation.

Optically active compounds can also be prepared by synthesis from a symmetrical compound in the presence of an optically active auxiliary compound. In such an asymmetric synthesis, the optically active auxiliary compound must form a bond, which may be covalent or complex, with the symmetrical compound. Consequently, the synthesis results in the formation of two diastereomers, which, because of their different energy content, may be formed in unequal amounts. A measure of the success of the asymmetric synthesis is the asymmetric induction $$\frac{A-B}{A+B} \cdot 100\,(\%),$$

which indicates the percentage excess of the preferentially formed diastereomer. A over the diastereomer B. After removing the optically active auxiliary compound, a mixture of the two enantiomers is obtained, in which one enantiomer now predominates and, under advantageous conditions, may even be virtually the sole product. The loss of the undesired enantiomer, which is a disadvantage in the case of racemate resolution, is thus reduced or even avoided.

An example of the above is the synthesis of optically active aminoacids which still have a hydrogen in the α-position, by hydrogenating α-aminoacrylic acid derivatives in the presence of optically active catalysts, which hydrogenation takes place with a high asymmetric induction (J. D. Morrisen et al., Asymmetric Organic Reactions, New Jersey, 1971). However, this method is not applicable to aminoacids which are completely substituted in the α-position, e.g. the pharmacologically important compounds α-methyl-DOPA and α-methyl-tyrosine. An attempt to obtain compounds of this type of asymmetric alkylation of α-isocyanocarboxylic acid menthyl esters followed by hydrolysis gives the aminoacid with an unsatisfactory asymmetric induction of at most 15% (M. Susuki et al., Chem. and Ind., (1972), 687).

We have found that 2-imidazolin-5-ones of the formula I

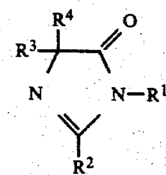

I where $R^1$ is an optically active radical corresponding to an amino compound $R^1NH_2$ which is a primary optically active amine or an optically active aminoacid or derivative thereof, $R^2$ is hydrogen, alkyl of 1 to 4 carbon atoms, benzyl or phenyl, $R^3$ and $R^4$ are different and $R^3$ is alkyl of 1 to 4 carbon atoms which may be unsubstituted or substituted by alkoxy, alkylthio or dialkylamino (where alkyl is in each case of 1 to 4 carbon atoms) or by benzyloxy, benzylthio, acyloxy (where acyl is of 1 to 4 carbon atoms), cyano, carbalkoxy (where alkyl is of 1 to 4 carbon atoms), benzoyl or phenyl, the phenyl ring in benzoyl or phenyl being unsubstituted or mono-, di- or tri-substituted by halogen, e.g. fluorine, chlorine, bromine or iodine, nitro, alkyl, alkoxy or alkylthio (where alkyl is in each case of 1 to 4 carbon atoms), benzyloxy, acyloxy or acylamino (where acyl is in each case of 1 to 4 carbon atoms) or monosubstituted by phenoxy (which is unsubstituted or substituted by alkoxy or acyloxy of 1 to 4 carbon atoms), trifluoromethyl or methylenedioxy, or $R^3$ is allyl or phenyl, and $R^4$ is alkyl of 1 to 6 carbon atoms which is unsubstituted or substituted by alkoxy, alkylthio or dialkylamino (where alkyl is in each case of 1 to 4 carbon atoms), piperidino, pyrrolidino, benzyloxy, benzylthio, cyano, carbalkoxy (where alkyl is of 1 to 4 carbon atoms), benzoyl or phenyl, the phenyl ring in benzoyl or phenyl being unsubstituted or mono-, di- or tri-substituted by halogen, e.g. fluorine, chlorine, bromine or iodine, nitro, alkyl, alkoxy or alkylthio (where alkyl is in each case of 1 to 4 carbon atoms), benzyloxy, acyloxy or acylamino (where acyl is in each case of 1 to 4 carbon atoms) or monosubstituted by phenoxy (which is unsubstituted or substituted by alkoxy or acyloxy of 1 to 4 carbon atoms), trifluoromethyl or methylenedioxy, or $R^4$ is pyridylmethyl, furylmethyl, thienylmethyl, naphthylmethyl, benzothienylmethyl, bromobenzofurylmethyl or allyl, are exceptionally suitable as intermediates for the synthesis of asymmetric compounds.

$R^1$ is an optically active radical based on $R^1NH_2$ which is an optically active primary amine or a derivative of an optically active α-aminoacid, advantageously an ester, in which the alcohol on which the ester is based is of 1 to 4 carbon atoms, or an amide, wherein the amide nitrogen is unsubstituted or is mono- or dialkylated with alkyl of 1 to 3 carbon atoms.

Examples of primary optically active amines are L- and D-α-phenylethylamine, L-α-phenyl-propylamine, (−)-nopinylamine, (+)- and (−)-aminomethylpinane, S-bornylamine, L(+)-threo-2-amino-1-phenyl-1,3-propanediol, (+)-dehydroabietylamine, (+)- and (−)-1-naphthyl-1-ethylamine, α-norbonylethylamine, menthylamine, norephedrin, β-methoxy-α-phenylethylamine, α-methoxy-β-phenylethylamine, (+)- and (−)-1-aminoindan, (+)- and (−)-amphetamine and (+)- and (−)-2-amino-1-butanol and examples of optically active aminoacid derivatives are L- and D-alanine esters, e.g. L-alanine tert.-butyl ester, L- and D-valine esters, e.g. L-valine isopropyl ester, L- and D-leucine esters, L-phenylalanine esters, e.g. L-phenylalanine ethyl ester, L- and D-α-methyl-β-(3,4-dimethoxyphenyl)-alanine ethyl esters, L- and D-serine esters, L- and D-cysteine esters, L- and D-glutamic acid diesters, L-glutamine esters, L- and D-aspartic acid diesters and L-asparagine esters.

As alkyl of 1 to 4 carbon atoms, $R^2$ may be, for example, methyl, ethyl, n-propyl, isopropyl, n-butyl, isobutyl and sec-butyl.

Examples of meanings of $R^3$ are:

as alkyl of 1 to 4 carbon atoms: methyl, ethyl, n-propyl, isopropyl, n-butyl, isobutyl and sec-butyl;

as substituted alkyl: methoxymethyl, α-methoxyethyl, ethoxymethyl, n-butoxymethyl, methylthiomethyl, β-methylthioethyl, ethylthiomethyl, δ-dimethylaminobutyl, benzyloxymethyl, α-benzyloxyethyl, benzylthiomethyl, β-benzylthioethyl, acetoxymethyl, α-acetoxyethyl, butyroxymethyl, cyanomethyl, carbomethoxymethyl, carbethoxymethyl, carbethoxyethyl, carbo-tert.-butoxymethyl, benzoylmethyl, p-bromobenzoylmethyl, benzyl, β-phenylethyl and α-phenylethyl;

as radicals containing substituted phenyl, especially benzyl: 2-, 3- and 4-methyl-, 4-ethyl-, 4-tert-butyl-, 4-methoxy-, 4-ethoxy-, 4-acetoxy-, 4-butyroxy-, 3,4-dimethoxy-, 3,4-diacetoxy-, 3-methoxy-4-acetoxy-, 3,4-dibenzyloxy-, 3,4-methylenedioxy-, 3,5-diiodo-4-acetoxy-, 3,5-diiodo-4-(p-methoxyphenoxy)-, 3,5-diiodo-4-(p-acetoxyphenoxy)-, 3-methoxy-, 4-nitro-, 4-acetamino-, 4-methylmercapto-, 3-chloro-4-methoxy-, 2-fluoro-, 4-fluoro-, 4-bromo-, 2-chloro-, 3-chloro-, 4-chloro-, 3-acetoxy-, 3-methoxy-4-chloro, 2,4-dimethoxy-, 2,4-diacetoxy-, 2-methyl-4-methoxy-, 3-methyl-4-methoxy-, 4-trifluoromethyl-, 3-methoxy-4-methyl-, 3-acetoxy-4-methyl-, 3-acetoxy-4-methoxy-, and 3,4,5-trimethoxy-phenyl and p-bromobenzoylmethyl.

Examples of meanings of $R^4$ are:

as alkyl of 1 to 6 carbon atoms: methyl, ethyl, propyl, butyl, pentyl and hexyl;

as substituted alkyl of 1 to 6 carbon atoms: methoxymethyl, ethoxymethyl, β-methoxyethyl, δ-methoxybutyl, β-methylthioethyl, β-dimethylaminoethyl, β-dipropylaminoethyl, γ-diethylaminopropyl, p-piperidinoethyl, γ-pyrrolidinopropyl, benzyloxymethyl, β-benzylthioethyl, cyanomethyl, carbomethoxymethyl, carbethoxymethyl, benzoylmethyl, p-bromobenzoylmethyl, benzyl, β-phenylethyl and benzyl;

as radicals containing substituted phenyl, especially benzyl: 2-, 3- and 4-methyl-, 4-ethyl-, 4-tert-butyl-, 4-methoxy-, 4-ethoxy-, 4-acetoxy-, 4-butyroxy-, 3,4-dimethoxy-, 3,4-diacetoxy-, 3-methoxy-4-acetoxy-, 3,4-dibenzyloxy-, 3,4-methylenedioxy-, 3,5-diiodo-4-acetoxy-, 3,5-diiodo-4-(p-methoxyphenoxy)-, 3,5-diiodo-4-(p-acetoxyphenoxy)-, 3-methoxy-, 4-nitro-, 4-acetamino-, 4-methylmercapto-, 3-chloro-4-methoxy-, 2-fluoro-, 4-fluoro-, 4-bromo-, 2-chloro-, 3-chloro-, 4-chloro-, 3-acetoxy-, 3-methoxy-4-chloro-, 2,4-dimethoxy-, 2,4-diacetoxy-, 2-methyl-4-methoxy-, 3-methyl-4-methoxy-, 4-trifluoromethyl-, 3-methoxy-4-methyl-, 3-acetoxy-4-methyl-, 3-acetoxy-4-methoxy- and 3,4,5-trimethoxy-phenyl.

Other meanings of $R^4$ are (naphth-1-yl)methyl, (naphth-2-yl)-methyl, (thien-2-yl)methyl, (benzothien-3-yl)methyl and (2-bromobenzofuran-3-yl)methyl.

Amongst the possible meanings of $R^1$ to $R^4$, the following should be singled out:

$R^1$: L-α-phenylethyl, (+)-3-pinyl-methyl, (−)-nopinyl and L-α-carbo-tert-butoxyethyl.

$R^2$: hydrogen, alkyl of 1 to 4 carbon atoms, especially methyl, benzyl or phenyl.

$R^3$: alkyl of 1 to 4 carbon atoms, e.g. methyl, ethyl, n-propyl, isopropyl, n-butyl and isobutyl, substituted alkyl of 1 to 4 carbon atoms, e.g. methoxymethyl, β-methylthioethyl, benzyloxymethyl, carbethoxymethyl and carbethoxyethyl, benzyl, which may be unsubstituted, or monosubstituted or disubstituted by alkoxy or acyloxy (where alkyl is in each case of 1 to 4 carbon atoms), or by benzyloxy, or monosubstituted by methylenedioxy, e.g. 3,4-dimethoxybenzyl, p-methoxybenzyl and 3,4-methylenedioxybenzyl, and phenyl.

$R^4$: alkyl of 1 to 4 carbon atoms, e.g. methyl, ethyl, propyl and butyl and substituted alkyl of 1 to 4 carbon atoms, e.g. methoxymethyl, β-methylthioethyl, benzyloxymethyl, cyanomethyl, carbomethoxymethyl, carbethoxymethyl, p-bromobenzoylmethyl, benzyl and substituted benzyl, as specified for $R^3$, e.g. 3,4-dimethoxybenzyl, p-methoxybenzyl, p-nitrobenzyl, o- and p-chlorobenzyl, p-bromobenzyl, 3,4-methylenedioxybenzyl and 3,4-dibenzyloxybenzyl, and allyl.

The following meanings are particularly preferred:

$R^1$: L-α-phenylethyl, $R^2$: hydrogen, $R^3$: methyl, or benzyl in which the phenyl part is unsubstituted or monosubstituted or disubstituted by alkoxy or acyloxy (in each case of 1 to 4 carbon atoms) or benzyloxy or monosubstituted by methylenedioxy, e.g. 4-methoxy-, 3,4-dimethoxy- and 3,4-methylenedioxy-benzyl, and $R^4$: methyl, or benzyl in which the phenyl part is unsubstituted or monosubstituted or disubstituted by alkoxy or acyloxy (in each case of 1 to 4 carbon atoms) or benzyloxy or monosubstituted by methylenedioxy, e.g. 4-methoxy-, 3,4-dimethoxy- and 3,4-methylenedioxy-benzyl.

The compounds according to the invention, of the formula I, can be prepared by reacting a 2-imidazolin-5-one of the formula II

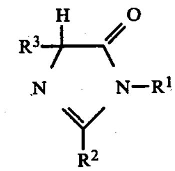

II where $R^1$ to $R^3$ have the above meanings, in a solvent or a solvent mixture, and in the presence of a base which converts a compound of the formula II to its anion, with an alkylating agent of the formula $R^4$—X, where $R^4$ has the above meanings and X is a radical which is easily removed in alkylation reactions.

The reaction can be illustrated by the following equation:

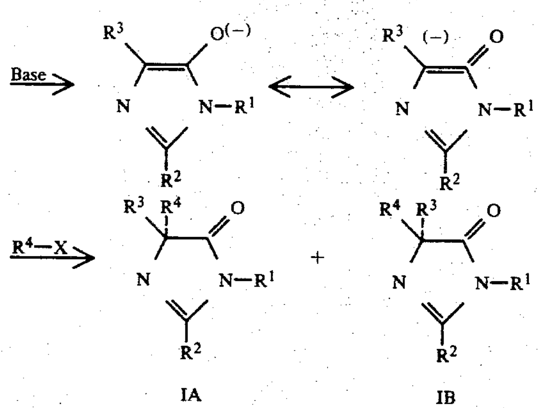

Which of the two diastereomers, namely IA or IB, is formed preferentially by the asymmetric induction, depends on the radical $R^1$. The process according to the invention provides the possibility of starting from a 2-imidazolin-5-one of the formula II which contains a radical $R^1$ which has the S- or R-configuration and obtaining the desired diastereomer IA or IB, that is to say of determining the steric position of the radical $R^4$ to be introduced.

Suitable solvents for the formation of the anion of the compound of the formula II and for the subsequent alkylation are those which are inert toward the base used and toward the alkylating agent used. Advantageous solvents are cyclic ethers, e.g. dioxane and tetrahydrofuran, dialkyl ethers, e.g. diethyl ether, aliphatic halohydrocarbons, e.g. methylene chloride, chloroform and carbon tetrachloride, carboxylic acid esters, e.g. ethyl acetate, benzene, alkylbenzenes and halobenzenes, e.g. toluene, xylene and chlorobenzene, dimethylformamide, dimethylsulfoxide, hexamethylphosphotriamide and mixtures of the above solvents.

Solvents to be singled out particularly are cyclic ethers, e.g. tetrahydrofuran, and halohydrocarbon, e.g. methylene chloride.

Bases to be used to convert a starting compound of the formula II into the anion are, advantageously, alkali metal or alkaline earth metal compounds, especially of lithium, sodium, potassium, magnesium and calcium, in which the metal is bonded to an aliphatic or aromatic hydrocarbon radical or to an acetylide group, or to the N atom of a primary or secondary amine or of ammonia, or in which the metal is in the form of the hydride, an alcoholate or the hydroxide. Further suitable bases are Grignard compounds and quaternary ammonium hydroxides.

Specific examples are butyl-lithium, phenyl-lithium, phenylsodium, sodium methanolate, sodium ethanolate, potassium tert.-butanolate, potassium amide, lithium diisopropylamide, sodium acetylide, phenyl-magnesium bromide, methyl-magnesium chloride, sodium hydride, calcium hydride, sodium hydroxide, potassium hydroxide, calcium hydroxide, triethylbenzylammonium hydroxide, tetrabutylammonium hydroxide and dimethyldibenzylammonium hydroxide.

Preferred bases to be used from amongst the above are alkali metal compounds of lithium, sodium and potassium, for example metal alkyls, e.g. butyllithium, alcoholates, e.g. sodium methanolate, sodium ethanolate and potassium tert.-butanolate, metal amides, e.g. lithium diisopropylamide, alkali metal hydroxides, e.g. sodium hydroxide and potassium hydroxide, and quaternary ammonium compounds, e.g. triethylbenzylammonium hydroxide, tetrabutylammonium hydroxide and dimethyldibenzylammonium hydroxide.

Alkylating agents for the purposes of the invention means compounds by means of which the radical $R^4$ can be introduced into metallized or anionized compounds of the formula II. In the alkylating agents $R^4$—X, where $R^4$ has the above meanings and especially the meanings singled out or particularly preferred, X as a rule is halogen, especially chlorine, bromine or iodine, or the radical of an appropriate organic sulfuric acid derivative, especially of a tosylate, benzenesulfonate or methanesulfonate.

Examples of advantageous and particularly preferred alkylating agents are methyl chloride, bromide, iodide and tosylate, benzyl chloride, bromide and tosylate, 4-methoxybenzyl chloride and bromide, 3,4-dimethoxybenzyl chloride, bromide and tosylate, 3,4-methylenedioxybenzyl chloride, bromide and tosylate, allyl chloride, bromide, iodide and tosylate, chloroacetonitrile, bromoacetonitrile, and methyl and ethyl chloroacetate and bromoacetate.

As a rule, the alkylation is carried out by employing the base and the alkylating agent advantageously in stoichiometric amounts or excess, in the solvent or solvent mixture employed. It is possible first to produce the anion and then to add the alkylating agent. However, it can also be advantageous to add the mixture of the starting compound and the alkylating agent to the base or to add the base to a mixture of the starting compound and alkylating agent.

The metallization and alkylation reactions are advantageously carried out at from −80° to +80° C., preferably at from −40° to +50° C.

It may be advantageous to carry out the reaction in the absence of atmospheric oxygen, for example under nitrogen.

In an advantageous embodiment of the alkylation, two-phase solvent mixtures, especially mixtures of water with a chlorohydrocarbon, e.g. methylene chloride, or a benzene hydrocarbon, e.g. benzene or toluene, or ethyl acetate, are used and the conventional methods of phase transfer catalysis, as described, for example, by M. Makosza in Pure Appl. Chem., 43 (1975), 439–462, are employed. The preferred bases are mixtures of an alkali metal hydroxide, especially sodium hydroxide, with a quaternary ammonium base or a phosphonium base, which is used, in the form of its halide, in catalytic amounts; examples of the second component are triethylbenzylammonium chloride, tetrabutylammonium bromide, dimethyldibenzylammonium chloride and tributylhexadecylphosphonium bromide.

Surprisingly, the alkylation of an anion of a 2-imidazolin-5-one of the formula II, which carries an optically active radical in the 1-position, leads, with a high degree of asymmetric induction, in some cases amounting to almost 100%, to the 2-imidazolin-5-ones, disubstituted in the 4-position, of the formula I. Furthermore, it was not foreseeable that the alkylation would take place virtually entirely at the carbon atom 4 and that no alkylation at the oxygen, such as might have been expected, is observed, particularly since the 2-imidazolin-5-ones of the formula II can, depending on the nature of the substituents, be entirely or partially in the enol form.

The particular importance of the compounds according to the invention is that aminoacids can be obtained by hydrolysis.

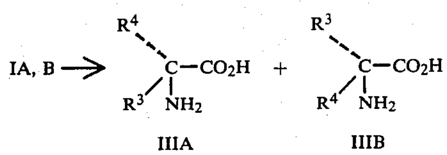

This provides a novel, advantageous and economical method of preparing optically active α-substituted aminoacids by asymmetric synthesis of a 2-imidazolin-5-one of the formula I followed by its hydrolysis, especially if an asymmetric induction of at least 20% has taken place during the preparation.

In addition to the compounds mentioned in the Examples, the following may be given as examples of compounds according to the invention, of the formula I: 1-L-α-phenylpropyl-2-isobutyl-4-ethyl-(m-methoxybenzyl)-2-imidazolin-5-one, 1-α-norbonylethyl-4-methyl-4-benzyl-2-imidazolin-5-one, 1-(L-α-phenyl-α-hydroxy-isopropyl)-4-methyl-4-(3′,4′-dimethoxybenzyl)-2-imidazolin-5-one, 1-(α-phenyl-β-methoxyethyl)-2,4-dibenzyl-4-isopropyl-2-imidazolin-5-one, 1-(α-hydroxy-sec.-butyl)-4-methyl-4-(3′,4′-dimethoxybenzyl)-2-imidazolin-5-one, 1-(L-α-carbo-tert.-butoxy-β-phenylethyl)-4-methyl-4-benzyl-2-imidazolin-5-one, 1-(L-α-3′,4′-dimethoxybenzyl-β-carboethoxyisopropyl)-4-methyl-4-(3′,4′-dimethoxybenzyl)-2-imidazolin-5-one, 1-(L-α-phenylethyl)-4-benzyl-4-methoxymethyl-2-imidazolin-5-one, 1-(L-α-phenylethyl)-4-benzyl-4-β-methylthioethyl-2-imidazolin-5-one, 1-(L-α-phenylethyl)-4-methyl-4-(3′,4′-diacetoxybenzyl)-2-imidazolin-5-one, 1-(L-α-phenylpropyl)-4-methyl-4-p-acetoxybenzyl-2-imidazolin-5-one, 1-(α-phenyl-β-methoxyethyl)-4-benzyl-4-β-dimethylaminoethyl-2-imidazolin-5-one and 1-(L-α-phenylpropyl)-4-methyl-4-(3′-methoxy-4′-acetoxybenzyl)-2-imidazolin-5-one.

The 2-imidazolin-5-ones of the formula II, possessing an optically active substituent on the nitrogen atom 1, have not been disclosed per se. However, they can readily be prepared in accordance with conventional methods described in the literature, as shown below:

1. By cyclizing a DL-α-aminoacid amide of the formula IV

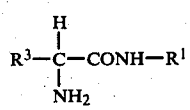

where $R^1$ and $R^3$ have the above meanings, with an orthocarboxylic acid ester of the general formula $R^2C(OR'')_3$, where $R^2$ has the above meanings and R″ is methyl or ethyl, at from 100° to 130° C., with elimination of alcohol, to give a 2-imidazolin-5-one of the general formula II. This process is described in the literature, for example by J. Brunken and G. Bach, Chem. Ber., 89 (1956), 1363 et seq. or by S. Ginsburg, J. org.-Chem., 27 (1962), 4062 et seq.

The DL-α-aminoacid amide of the formula IV which is used can be obtained by reacting a DL-α-aminoacid ester of the general formula V

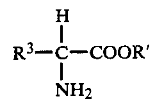

where $R^3$ has the above meaning and R′ is methyl or ethyl, with an optically active amine of the formula $R^1$—$NH_2$, where $R^1$ has the above meanings, by a conventional process, as described, for example, by J. Brunken and B. Bach in Chem. Ber. 89 (1956), 1363 et seq.

2. It has been disclosed, for example in Ber. dt. Chem. Ges. 47 (1914), 2545 et seq., that imido-acid esters of the general formula

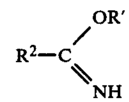

where $R^2$ has the above meanings and R′ is methyl or ethyl, can be reacted with an α-aminoacid ester to give a condensation product of the general formula VI, where $R^2$ and $R^3$ have the above meanings and R′ is methyl or ethyl

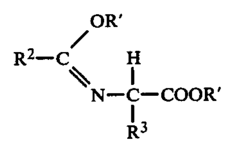

and this compound, in turn, can be cyclized with an amine of the general formula $R^1$—$NH_2$ to give a 2-imidazolin-5-one of the formula II, as described, for example, in J. Chem. Soc., 1959, 1648 et seq.

3. 2-Imidazolin-5-ones of the formula II which are unsubstituted in the 2-position, i.e., where $R^2$ is H, may be obtained by reacting an α-substituted isocyanoacetic acid ester of the formula VII

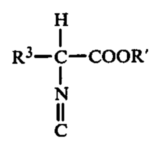

where $R^3$ has the above meaning and R′ is methyl or ethyl, with an optically active amine $R^1$—$NH_2$, where $R^1$ has the above meaning, to give an isocyanoacetic acid amide of the general formula VIII

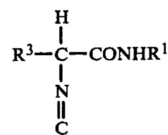

where $R^1$ and $R^3$ have the above meanings, which, on conversion to the anion by treatment with a base, cyclizes spontaneously to a 2-imidazolin-5-one of the formula II, where $R^2$ is hydrogen.

For this purpose, a compound of the formula VIII is reacted with a base under the conditions described above for the production of the anion of a compound of the formula II, and an equimolar amount of an acid is then added.

The compounds of the formula VIII can also be obtained by reacting an N-formylaminoacid with an optically active amine of the formula $R^1$—$NH_2$, where $R^1$ has the above meanings, in the presence of triphenylphosphine and carbon tetrachloride.

4. 2-Imidazolin-5-ones of the formula II, especially those where $R^3$ is benzyl or substituted benzyl and which carry phenyl or benzyl radicals in the 2-position, can be prepared in accordance with conventional methods from the corresponding oxazolinones of the formula IX, where $R^2$ is phenyl or benzyl and Ar is phenyl or substituted phenyl

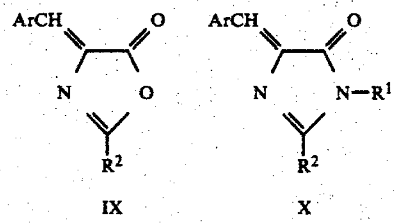

by reaction with an optically active amine $R^1$—$NH_2$, where $R^1$ has the above meaning.

This method is described, for example, in publication in Indian J. Chem. 9 (1975), 789 et seq. and Aust. J. Chem. 26 (1973), 827 et seq. and 1701 et seq. After hydrogenating the intermediate X by conventional methods, for example in the presence of catalytic amounts of platinum or palladium, as described, for example, in J. Org. Chem. 27 (1962), 4527 et seq., the corresponding 2-imidazolin-5-ones II are obtained.

An advantageous variant of the method of preparation of the compounds according to the invention, of the formula I, is to cyclize an α-substituted isocyanoacetic acid amide of the formula VIII directly with a base under the above conditions to give the anion of a 2-imidazolin-5-one of the formula II, where $R^2$ is hydrogen, and then to react the anion obtained with an alkylating agent in the manner described above.

We have established that the asymmetric induction found is independent of whether a previously prepared and isolated 2-imidazolin-5-one of the formula II or a corresponding α-substituted isocyanoacetic acid amide of the formula VIII is used as the starting material.

An anionized 2-imidazolin-5-one of the formula II can also be obtained by converting an unsubstituted isocyanoacetic acid amide of the formula XI

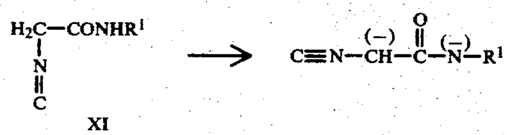

where $R^1$ has the above meaning, into the dianion by reaction with 2 equivalents of a base, especially of an organo-metallic compound or of a dialkylamide, and monoalkylating the dianion stepwise with one equivalent of an alkylating agent of the formula $R^3$—X, where $R^3$ and X have the above meanings, whereupon spontaneous cyclization occurs and an anion of the formula II is obtained. Thereafter, alkylation is carried out with an alkylating agent of the formula $R^4$—X, using the method described above, to give a compound of the formula I.

The advantage of this method is that both substituents, $R^3$ and $R^4$, are introduced by means of an alkylating reaction which takes place readily, so that the process can be varied very easily.

The preferred use of the compound according to the invention, of the formula I, is for the preparation of optically active aminoacids. Accordingly, the present invention also relates to a process for the preparation of optically active aminoacids, wherein a diastereomer mixture, obtained by asymmetric induction, of a chirally substituted 2-imidazolin-5-one of the formula I is hydrolyzed in the conventional manner in a solvent or solvent mixture in the presence of an acid or alkali.

The preferred embodiment is a process for the preparation of optically active α-methyl-aryl-alanines, wherein a diastereomer mixture, obtained by asymmetric induction, of a chirally substituted 2-imidazolin-5-one of the formula I

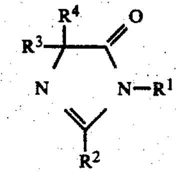

I ps where $R^1$ is an optically active radical corresponding to an amino compound $R^1NH_2$ which is a primary optically active amine or an optically active aminoacid or derivative thereof, $R^2$ is hydrogen, alkyl of 1 to 4 carbon atoms, benzyl or phenyl, $R^3$ and $R^4$ are different and $R^3$ is methyl or is benzyl which is unsubstituted or is monosubstituted or disubstituted by alkoxy or acyloxy of 1 to 4 carbon atoms or benzyloxy or is monosubstituted by methylenedioxy and $R^4$ is methyl or is benzyl which is unsubstituted or is monosubstituted or disubstituted by alkoxy or acyloxy of 1 to 4 carbon atoms or benzyloxy or is monosubstituted by methylenedioxy, is hydrolyzed in a solvent or solvent mixture in the presence of an acid or alkali.

Amongst the above meanings of $R^1$ and $R^2$, $R^1$ is especially L-α-phenylethyl, (+)-3-pinyl-methyl, (−)-nopinyl or L-α-carbo-tert.-butoxyethyl and $R^2$ is especially hydrogen or methyl; the case where $R^1$ is L-α-phenylethyl and $R^2$ is hydrogen is particularly preferred.

Examples of substituted benzyl radicals $R^3$ and $R^4$ are 4-methoxybenzyl, 4-ethoxybenzyl, 4-acetoxybenzyl, 4-butyroxybenzyl, 3,4-dimethoxybenzyl, 3,4-methylenedioxybenzyl, 3,4-dibenzyloxybenzyl, 3,4-diacetoxybenzyl, 3-methoxy-4-acetoxybenzyl and 3-acetoxy-4-methoxybenzyl, amongst which 4-methoxybenzyl, 3,4-dimethoxybenzyl and 3,4-methylenedioxybenzyl are preferred.

Advantageous solvents to use for the hydrolysis are water, lower monohydric or dihydric alcohols of 1 to 4 carbon atoms, e.g. methanol, ethanol, n-butanol, ethylene glycol or ethylene glycol monoethers, e.g. 2-ethoxyethanol, or aprotic solvents, for example cyclic saturated ethers, e.g. tetrahydrofuran or dioxane, or dimethylsulfoxide, or mixtures of these solvents, especially mixtures with water.

Preferred solvents are water, lower monohydric alcohols, especially methanol and ethanol, ethylene glycol and cyclic saturated ethers, esepcially tetrahydrofuran and dioxane. Preferred solvent mixtures are aqueous-alcoholic mixtures, especially water/methanol and water/ethanol.

The acids used for the hydrolysis are strong monobasic or polybasic inorganic hydro-acids such as hydrohalic acids, e.g. hydrogen chloride or hydrogen bromide, sulfuric acid or phosphoric acid. The bases used are, in particular, alkali metal hydroxides, e.g. sodium hydroxide or potassium hydroxide. For alkaline hydrolysis, ethanol/water and glycol/water have proved particularly expedient as solvent mixtures.

The hydrolysis is advantageously carried out at elevated temperatures, i.e. at from 50° to 150° C. As a rule, it is carried out at the boiling point of the particular solvent or solvent mixture; however, it can also be carried out by heating the mixture at from 50° to 150° C. in an autoclave.

In some cases it may prove advantageous first to prepare the aminoacid ester by treatment with an anhydrous acid, for example a hydrohalic acid, e.g. hydrogen chloride or hydrogen bromide, or with sulfuric acid, in an alcohol; the ester can then, if required, be hydrolyzed in the conventional manner. The hydrolysis may also give the aminoacid amide, which is then hydrolyzed to the desired acid.

The course of the hydrolysis can readily be followed, and its end determined, by thin layer chromatography.

During the hydrolysis, the optically active amine used for the synthesis of the compound I is recovered and can be reused. This is a particular advantage of the process according to the invention for asymmetric syntheses.

If the preparation of the starting compounds of the formula I takes place with quantitative or almost quantitative asymmetric induction, the aminoacid obtained after hydrolysis is virtually optically pure. In other cases, purification may be necessary. This purification or resolution may already be carried out on the diastereomer mixture of the intermediates of the formula I. In general, resolution can be effected by recrystallization, alcohol and ether being advantageous solvents; alternatively, the resolution is carried out in the conventional manner, for example by selective crystallization, on the enantiomer mixture of the aminoacids obtained by hydrolysis.

Particular examples of optically active aminoacids which can be prepared from the compounds according to the invention, of the formula I, are L-α-methyl-β-(3,4-dihydroxyphenyl)-alanine, L-α-methylphenylalanine and L-α-methyl-β-(p-hydroxyphenyl)-alanine.

α-Methyl-β-(3,4-dihydroxyphenyl)-alanine, referred to as α-methyl-DOPA, has proved a powerful anti-hypertensive agent in humans. α-Methyl-β-p-hydroxyphenyl-alanine, referred to as α-methyltyrosine, is a promising tranquilizer. With these compounds, as with most aminoacids which have an asymmetric carbon atom, it is the L-form which is active. The D-form is inactive as an anti-hypertensive agent or tranquilizer, but is as toxic as the L-form.

EXAMPLES

In the Examples in which the asymmetric induction is stated, the latter is calculated from the ratio of the diastereomers IA and IB, which is easily determined by NMR spectroscopy, since the diastereomers, being physically different species, exhibit different chemical shifts for certain protons. The correctness of the allocation can be proved by converting the diastereomer mixture of the imidazolinone I by hydrolysis into the enantiomer mixture of the aminoacid, determining the optical rotation of this mixture and comparing it with that of the pure, preferentially formed, enantiomer.

A. PREPARATION OF STARTING COMPOUNDS

1. α-Isocyanopropionic acid L-α-phenylethylamide (a) from methyl α-isocyanopropionate:

11.3 g (0.1 mole) of methyl α-isocyanopropionate, 12.1 g (0.1 mole) of L-α-phenylethylamine and 0.1 g of p-toluenesulfonic acid are stirred for 12 hours at room temperature. The mixture is then heated at 100° C. for 30 minutes and the amide obtained is purified by recrystallization from methanol. 16.4 g (81%) of α-isocyanopropionic acid L-α-phenylethylamide of melting point 89° C. are obtained.

IR spectrum (KBr): 3,300 (N—H), 2,140 (N═C) and 1,665 $cm^{-1}$ (C═O).

$C_{12}H_{14}N_2O$(202): Calculated: C 71.3; H 7.0. Found: C 71.1; H 6.9.

(b) from N-formyl-α-alanine 1.17 g (10 mmoles) of N-formyl-α-alanine, 1.33 g (11 mmoles) of L-α-phenylethylamine and 3.15 g (12 mmoles) of triphenylphosphine are dissolved in 20 ml of acetonitrile. 2.0 g (20 mmoles) of triethylamine and 1.54 g (10 mmoles) of carbon tetrachloride are added thereto, whilst stirring. The mixture is stirred for 5 hours at room temperature, a solution of 3.15 g (12 mmoles) of triphenylphosphine in 5 ml of acetonitrile is added and a mixture of 1.54 g (10 mmoles) of carbon tetrachloride and 1.0 g (10 mmoles) of triethylamine is then introduced dropwise. After 12 hours, the triethylamine hydrochloride which has precipitated is filtered off and the solvent is distilled off. The residue is purified by column chromatography over silica gel, using ether. After recrystallization from methanol, 1.2 g (60%) of α-isocyanopropionic acid α-phenylethylamide of melting point 89° C. are obtained.

2. α-Alanine-L-α-phenylethylamide 42.0 g (0.3 mole) of DL-alanine methyl ester hydrochloride are introduced into 108.0 g (0.9 mole) of L-α-phenylethylamine at room temperature and the mixture is heated for 3 hours at 95°-100° C. whilst stirring. It is cooled, 250 ml of absolute ethanol are added, 27.0 g (0.33 mole) of sodium acetate are then introduced and the mixture is stirred for 45 minutes at room temperature. The ethanol is then stripped off and the residue is taken up in methylene chloride and rendered alkaline with a solution of 13.2 g (0.33 mole) of sodium hydroxide in 90 ml of water. After repeated extraction by shaking with methylene chloride, the combined organic phases are dried over anhydrous sodium sulfate, the solvent is distilled off and the excess L-α-phenethylamine is distilled off under 15 mm Hg. The fraction (90.2 g) which passes over at 78°-85° C. is pure L-α-phenylethylamine, which can be re-used for further reactions. The semi-crystalline distillation residue (28.2 g=49.0% of theory) is pure according to NMR spectroscopy.

$^1$H-NMR ($CDCl_3$): $\tau$=2.33 (broad, CONH), 2.85 (Ph—H), (9, J=7.0 Hz, CH), 6.62 (9, J=7.0 Hz, CH), 8.37 ($NH_2$), 8.56 (d, J=7.0 Hz, $CH_3$), 8.75 (d, J=7.0 Hz, $CH_3$.

3. α-Isocyanopropionic acid (+)-3-pinylmethylamide

A mixture of 5.7 g (50 mmoles) of methyl α-isocyanopropionate and 8.3 g (50 mmoles) of (+)-3-aminomethylpinane is stirred for 15 hours at room temperature, initially with slight cooling. After distilling off the resulting methanol in a high vacuum at 80° C., 11.6 g of crystalline α-isocyanopropionic acid (+)-3-pinylmethylamide of melting point 58°-59° C. remain. IR spectrum (KBr): 3,230 (N—H), 2,130 (N≡C), 1,670 $cm^{-1}$ (C═O).

4. DL-Alanine-(+)-3-pinylmethylamide 1.40 g (0.1 mole) of α-alanine methyl ester hydrochloride are introduced into 50.2 g (0.3 mole) of (+)-3-aminomethyl-pinane and the mixture is heated for 3 hours at 95°-100° C. When it has cooled, 100 ml of absolute ethanol are added, 9.0 g (0.11 mole) of sodium acetate are introduced and the batch is stirred for 45 minutes at room temperature. The ethanol is then distilled off and the residue is taken up in methylene chloride and rendered alkaline with a solution of 4.4 g (0.11 mole) of sodium hydroxide in 30 ml of water. The mixture is repeatedly extracted with methylene chloride, the extract is dried over anhydrous sodium sulfate and the solvent is distilled off. The excess (+)-3-aminomethyl-pinane is distilled from the residue at 110° C. under 15 mm Hg. 28.6 g are recovered. The crude product which remains, in a yield of 70%, can be employed, without additional purification, for the cyclization reactions which follow.

$^1$HNMR ($CDCl_3$) τ=2.41 (broad, CONH)

5. α-Isocyanopropionic acid (−)-nopinylamide

A mixture of 5.7 g (50 mmoles) of methyl α-isocyanopropionate and 7.0 g (50 mmoles) of (−)-nopinylamine is stirred for 15 hours at room temperature, initially employing slight cooling. After removing the resulting methanol in a high vacuum at 80° C., 9.8 g of crystalline α-isocyanopropionic acid (−)-nopinylamide remain. Melting point 114°-115° C. (after recrystallization from isopropanol).

IR spectrum (KBr): 3,310 (N—H), 2,130 (N≡C), 1,655 $cm^{-1}$ (C═O).

$C_{13}H_{20}N_2O$ (220): Calculated: C 70.8; H 9.1; N 12.7. Found: C 70.8; H 9.2; N 12.7.

6. α-Isocyano-β-phenyl-propionic acid L-α-phenylethylamide 18.9 g (0.1 mole) of methyl α-isocyano-β-phenylpropionate and 12.1 g (0.1 mole) of L-α-phenylethylamine are heated for 12 hours at 60° C. After removing the resulting methanol in a high vacuum at 60° C., 26.5 g of amide remain. Melting point 135°-136° C. (after recrystallization from isopropanol).

IR-spectrum (KBr): 3,290 (N—H), 2,150 (C≡N), 1,665 $cm^{-1}$ (C═O).

$C_{18}H_{18}N_2O$ (278): Calculated: C 77.7; H 6.5; N 10.1. Found: C 77.5; H 6.6; N 10.3.

7. Isocyanoacetic acid L-α-phenylethylamide 9.9 g (0.1 mole) of methyl isocyanoacetate are slowly added dropwise, at +10° C., to 12.1 g (0.1 mole) of L-α-phenylethylamine. When the slightly exothermic reaction has ended, the mixture is heated for 2 hours at 30°-35° C. and the resulting methanol is then removed in a high vacuum at 60° C. Recrystallization from ethyl acetate gives 15.0 g of isocyanoacetic acid L-α-phenylethylamide of melting point 122°-123° C.

$C_{11}H_{12}N_2O$ (188): Calculated: C 70.2; H 6.4; N 14.9. Found: C 70.0; H 6.2; N 15.2.

8. N-(α-Isocyano-propionyl)-L-alanine tert.-butyl ester 1.13 g (10 mmoles) of methyl α-isocyanopropionate are stirred with 1.45 g (10 mmoles) of L-alanine tert.-butyl ester and a pinch of p-toluenesulfonic acid at 50° C. overnight. The mixture is then chromatographed over 100 g of alumina of activity level II, using ether. 1.4 g (60%) of product are obtained.

$^1$H-NMR (60 MHz, $CDCl_3$): τ=8.5 (s, tert.-butyl, 5.53 (mc, both CH), 2.7 (mc, NH).

IR (film): ν=1,680 (amide C═O), 1,735 (ester C═O), 2,140 (N≡C), 3,305 $cm^{-1}$ (N—H).

$C_{11}H_{18}N_2O_3$ (226.3): Calculated: C 58.39; H 8.02. Found: C 58.5; H 8.0.

B. PREPARATION OF COMPOUNDS OF THE FORMULA II 1. 1-L-α-Phenylethyl-4-methyl-2-imidazolin-5-one 9.4 ml of a 1.6 N solution of n-butyl-lithium (15 mmoles) in hexane are added dropwise to a solution of 3.1 g (15 mmoles) of α-isocyanopropionic acid L-α-phenylethylamide in 20 ml of tetrahydrofuran at −60° C. The mixture is allowed to rise to −20° C. and is neutralized, at this temperature, by adding 0.9 g (15 mmoles) of glacial acetic acid in 5 ml of tetrahydrofuran. The solvent is distilled off on a rotary evaporator and the residue is partitioned between methylene chloride and water. The organic phase is concentrated. After distilling the residue, 2.05 g (65%) of 1-L-α-phenylethyl-4-methyl-2-imidazolin-5-one of boiling point 105° C./$10^{-3}$ mm Hg are obtained.

IR spectrum (film): 1,610 (C═N), 1,715 $cm^{-1}$ (C═O).

$C_{13}H_{14}N_2O$ (202): Calculated: C 71.3; H 7.0. Found: C 71.1; H 6.9.

2. 1-L-α-Phenylethyl-4-methyl-2-imidazolin-5-one 63.6 g (0.6 mole) of trimethyl orthoformate are added to 26.2 g (0.135 mole) of α-alanine-L-α-phenylethylamide and the mixture is heated for 2 hours at 85° C. and then for 1 hour at 120° C., the methanol thus formed being distilled off. The reaction product is freed from excess trimethyl ortho-formate on a rotary evaporator and the residue is distilled under reduced pressure. 10.5 g (38.5% of theory) of 1-L-α-phenylethyl-4-methyl-2-imidazolin-5-one of boiling point 129°-133° C./0.1 mm Hg and melting point 43°-44° C. are obtained.

$C_{12}H_{14}NO_2$ (202.3): Calculated: N 13.85. Found: N 13.9.

According to the IR and NMR spectra the compound is identical with the product obtained as described in Example B. 1.

3. 2,4-Dimethyl-1-L-α-phenylethyl-2-imidazolin-5-one 120 g (1 mole) of trimethyl orthoacetate are added to 56.4 g (0.293 mole) of α-alanine-L-α-phenylethylamide, the mixture is heated for 4 hours at 85° C. and then for 1 hour at 120° C. and the methanol which is eliminated is distilled off. After cooling, the excess trimethyl orthoacetate is distilled off on a rotary evaporator and the residue is distilled under reduced pressure. 37.25 g, i.e. 58.7% of theory, of a product of boiling point 139°-141° C./0.4 mm Hg are obtained.

IR (film): 1,720 $cm^{-1}$ (C=O), 1,630 $cm^{-1}$ (C=N).

$^1$H-NMR ($COCl_3$): τ=2.90 (Ph—H), 4.78 (q, J=z, 0 Hz, CH), 6.13 (q, J=7.5 Hz, CH), 8.19 (d, J=2.0 Hz, $CH_3$), 8.33 (d, J=7.0 Hz, $CH_3$), 8.67 (dd, J=2.0 and 7.5 Hz, $CH_3$).

4.

2-Methyl-4-benzyl-1-L-α-phenylethyl-2-imidazolin-5-one (a) DL-Phenylalanine-L-α-phenylethylamide 64.7 g (0.3 mole) of DL-phenylalanine methyl ester hydrochloride and 108.0 g (0.9 mole) of L-α-phenylethylamine are reacted, and worked up, as described in Example A. 2. 42.7 g (53.4% of theory) of DL-phenylalanine-L-α-phenylethylamide are obtained, and are directly reacted further.

(b) 2-Methyl-4-benzyl-1-L-α-phenylethyl-2-imidazolin-5-one 21.3 g (80 mmoles) of DL-phenylalanine-L-α-phenylethylamide and 30.0 g (0.25 mole) of trimethyl orthoacetate are reacted, and worked up, as described in Example B. 3. 7.9 g (33.8% of theory) of the desired product of boiling point 160°-170° C./0.2 mm Hg are obtained.

IR (film): 1,725 $cm^{-1}$ (C=O), 1,635 $cm^{-1}$ (C=N).

$^1$H-NMR: τ=2.63 and 2.70 (Ph—H), 4.72 (q, J=7.0 Hz, CH), 5.62 (dt, J=2.0 Hz and 5.0 Hz, CH), 6.70 (t, J=5.0 Hz, $CH_2$), 8.28 (dd, J=5.0 and 2.0 Hz, $CH_3$), 8.40 (d, I=7.0 Hz, $CH_3$).

5. 4-Methyl-1-[(+)-3'-pinylmethyl]-2-imidazolin-5-one 16.6 g (70 mmoles) of α-alanine-(+)-3-pinylmethylamide and 21.2 g (0.2 mole) of trimethyl orthoformate are reacted, and worked up, as described in Example B. 2. After distillation under reduced pressure, 9.0 g (50.8% of theory) of the desired product, of boiling point 144°-148° C./0.1 mm Hg, are obtained.

6. 1-L-α-Phenylethyl-4-isobutyl-2-imidazolin-5-one 15.5 g (0.1 mole) of methyl 2-isocyano-4-methyl-valerate (boiling point 56°-58° C./0.3 mm Hg) and 12.1 g (0.1 mole) of L-α-phenylethylamine are heated to 80° C. in the course of 1 hour and stirred for 5 hours at this temperature. Methanol and unconverted starting compounds are then distilled off by heating to 100° C. under reduced pressure (0.1 mm Hg). 12.4 g of 1-L-α-phenylethyl-4-isobutyl-2-imidazolin-5-one remain; according to the NMR and IR spectra, this product is a keto-enol mixture.

C. PREPARATION OF COMPOUNDS OF THE FORMULA I

1.

1-L-α-phenylethyl-4-methyl-4-benzyl-2-imidazolin-5-one 62.5 ml of a 1.6 N solution of n-butyl-lithium (0.1 mole) in hexane are added dropwise to a solution of 20.2 g (0.1 mole) of α-isocyanopropionic acid L-α-phenylethylamide in 125 ml of tetrahydrofuran at −60° C. At the same temperature, 17.1 g (0.1 mole) of benzyl bromide dissolved in 50 ml of tetrahydrofuran are added dropwise to the pale yellow solution and the mixture is allowed to come to room temperature, whilst stirring. The solvent is distilled off, the residue is taken up in 150 ml of methylene chloride and the solution is washed with twice 100 ml of water. After distilling off the solvent, 27.5 g of crystalline 1-L-α-phenylethyl-4-methyl-4-benzyl-2-imidazolin-5-one remain.

Analysis of the NMR spectrum (220 MHz, $CDCl_3$) shows that the product contains at least 95% of pure diastereomer. Melting point (after recrystallization from methylene chloride/ether) 110° C.

IR spectrum (KBr): 1,610 (C=N), 1,715 $cm^{-1}$ (C=O).

$C_{19}H_{20}N_2O$ (292): Calculated: C 78.1; H 6.9. Found: C 78.1; H 6.9.

2.

1-L-α-Phenylethyl-4-methyl-4-benzyl-2-imidazolin-5-one

In an experiment similar to that in Example C. 1., potassium tert.-butanolate is employed instead of n-butyl-lithium. According to analysis of the NMR spectrum (220 MHz, $CDCl_3$), the crude 1-L-α-phenyl-ethyl-4-methyl-4-benzyl-2-imidazolin-5-one obtained consists of a mixture of the diastereomers in the ratio of 95:5, which corresponds to an asymmetric induction of 90%.

3.

1-L-α-Phenylethyl-4-methyl-4-benzyl-2-imidazolin-5-one

In an experiment similar to that in Example C. 1., sodium methanolate is employed instead of butyl-lithium. The benzyl bromide is added dropwise at +50° C. According to analysis of the NMR spectrum (220 MHz, $CDCl_3$) the crude 1-L-α-phenylethyl-4-methyl-4-benzyl-2-imidazolin-5-one obtained consists of a mixture of the diastereomers in the ratio of 76:24, corresponding to an asymmetric induction of 52%.

4.

1-L-α-Phenylethyl-4-methyl-4-benzyl-2-imidazolin-5-one

A solution of 2.05 g (10 mmoles) of 1-L-α-phenylethyl-4-methyl-2-imidazolin-5-one and 1.3 g (10 mmoles) of benzyl chloride in 10 ml of methylene chloride is added dropwise in the course of 30 minutes, at from 10° to 20° C., to a vigorously stirred mixture of 20 g of 50% strength sodium hydroxide solution and 10 ml of methylene chloride, to which 100 mg of triethylbenzylammonium chloride are added as a phase transfer catalyst. The mixture is stirred for a further 2 hours at room temperature, the two phases are separated and the methylene chloride solution is washed with water and dried by means of sodium sulfate. After distilling off the solvent, 2.8 g of 1-L-α-phenylethyl-4-methyl-4-benzyl-2-imidazolin-5-one remain. Analysis of the NMR spectrum (220 MHz, $CDCl_3$) shows a ratio of the diastereomers of 84:16 (asymmetric induction 68%).

5.

1-L-α-Phenylethyl-2,4-dimethyl-4-benzyl-2-imidazolin-5-one

A solution of 4.4 g (20 mmoles) of 1-L-α-phenylethyl-2,4-dimethyl-2-imidazolin-5-one in 30 ml of tetrahydrofuran is metallated with butyl-lithium by the method described in Example C. 1. and is then reacted with benzyl bromide. After working up as described, 5.9 g of crude 1-L-α-phenylethyl-2,4-dimethyl-4-benzyl-2-imidazolin-5-one remain. Analysis of the NMR spectrum (220 MHz, $CDCl_3$) shows a ratio of the diastereomers of 73:27 (asymmetric induction 46%).

The diastereomer which is formed in excess is separated off by column chromatography (silica gel, methylene chloride, ethyl acetate) and recrystallized from petroleum ether.

Melting point 108°-109° C.

IR spectrum (KBr): 1,710 (C=O), 1,635 $cm^{-1}$ (C=N).

$C_{20}H_{22}N_2O$ (306): Calculated: C 78.5; H 7.2; N 9.2. Found: C 78.5; H 7.2; N 9.4.

6.

1-L-α-Phenylethyl-2,4-dimethyl-4-benzyl-2-imidazolin-5-one

Potassium tert.-butanolate or sodium methanolate is employed in place of n-butyl-lithium in experiments similar to those described in Example C. 5. The following results are obtained:

| Base | Reaction temperature | Diastereomer ratio | Asymmetric induction |
|---|---|---|---|
| $KOC_4H_9$ | −40° C. | 70:30 | 40% |
| $NaOCH_3$ | −40° C. | 65:35 | 30% |

7.

1-L-α-Phenylethyl-2,4-dimethyl-4-benzyl-2-imidazolin-5-one 2.6 g (22 mmoles) of 95% strength potassium tert.-butanolate are introduced into a solution of 5.8 g (20 mmoles) of 1-L-α-phenylethyl-2-methyl-4-benzyl-2-imidazolin-5-one in 40 ml of tetrahydrofuran at −30° C. The mixture is stirred for 10 minutes at 0° C. and cooled to −65° C., and a solution of 1.9 g (20 mmoles) of methyl bromide in 8 ml of tetrahydrofuran is added dropwise. The mixture is worked up as described in Example C. 1. and 5.4 g of crude 1-L-α-phenylethyl-2,4-dimethyl-4-benzyl-2-imidazolin-5-one are obtained.

Analysis of the NMR spectrum (220 MHz, $CDCl_3$) shows a ratio of the diastereomers of 42:58, the diastereomer formed preferentially in the present case corresponding to the diastereomer formed in the minor proportion in Examples C. 5. and C 6. The reversal of the reaction sequence (in C. 5. and C. 6. the 4-methyl substituent was present first and benzyl was introduced whilst in the present Example the 4-methyl substituent is present first and methyl is introduced) also results in an inversion of the diastereomer ratio.

8.

1-(+)-3′-Pinylmethyl-4-methyl-4-benzyl-2-imidazolin-5-one 1.3 g (11 mmoles) of 95% strength potassium tert.-butanolate are introduced into a solution of 2.5 g (10 mmoles) of α-isocyanopropionic acid (+)-3-pinylmethylamide in 20 ml of tetrahydrofuran at −30° C. The mixture is stirred for 10 minutes at 0° C. and is cooled to −65° L C., and 1.75 g (10 mmoles) of benzyl bromide are added dropwise. The batch is worked up as described in Example C. 1. and 3.3 g of crude 1-(+)-3′-pinylmethyl-4-methyl-4-benzyl-2-imidazolin-5-one, melting point 96°-98° C., are obtained.

Analysis of the NMR spectrum (220 MHz, $CDCl_3$) shows a ratio of the diastereomers of 57:43.

IR spectrum (KBr): 1,710 (C=O), 1,610 $cm^{-1}$ (C=N).

$C_{22}H_{30}N_2O$ (338): Calculated: C 78.1; H 8.9; N 8.3. Found: C 78.1; H 8.9; N 8.5.

9. 1-(−)-Nopinyl-4-methyl-4-benzyl-2-imidazolin-5-one 6.5 g (55 mmoles) of 95% strength potassium tert.-butanolate are introduced into a solution of 11.0 (50 mmoles) of α-isocyanopropionic acid (−)-nopinylamide in 100 ml of tetrahydrofuran at −30° C. The mixture is stirred for 10 minutes at 0° C. and is cooled to −65° C., and 8.8 g (50 mmoles) of benzyl bromide are added dropwise. The batch is worked up as described in Example C 1. and 15.5 g of crude crystalline 1-(−)-nopinyl-4-methyl-4-benzyl-2-imidazolin-5-one are obtained.

Analysis of the NMR spectrum (220 MHz, $CDCl_3$) shows a ratio of the diastereomers of 75 to 25.

The diastereomer which is formed in excess is isolated by recrystallization from isopropanol, melting point 150° C.

IR spectrum (KBr): 1.705 (C=O), 1,600 $cm^{-1}$ (C=N).

$C_{20}H_{26}N_2O$ (310): Calculated: C 77.4; H 8.4; N 9.0. Found: C 77.1; H 8.2; N 8.9.

10.

1-L-α-Phenylethyl-4-methyl-4-(3′,4′-dimethoxybenzyl)-2-imidazolin-5-one 6.2 ml (10 mmoles) of a 1.64 N solution of butyl-lithium in hexane are added dropwise to a solution of 2.05 g (10 mmoles) of α-isocyanopropionic acid L-α-phenylethylamide in 2.0 ml of tetrahydrofuran at −65° C. 1.9 g (10 mmoles) of 3,4-dimethoxybenzyl chloride are then added and the mixture is stirred for 3 hours at +40° C.

The solvent is distilled off. The residue is partitioned between methylene chloride and water and the methylene chloride solution is evaporated to dryness. 3.6 g of crude 1-L-α-phenylethyl-4-methyl-(3′,4′-dimethoxybenzyl)-2-imidazolin-5-one, which crystallize on scratching, remain.

Analysis of the NMR spectrum (220 MHz, $CDCl_3$) shows a ratio of the diastereomers of 80:20, which corresponds to an asymmetric induction of 60%.

The diastereomer formed in excess is isolated by suspension in ether and is recrystallized from isopropanol; melting point 99°-100° C.

IR spectrum: 1,603 (C=N), 1,705 $cm^{-1}$ (C=O).

$C_{21}H_{24}N_2O_3$ (352): Calculated: C 71.6%; H 6.8%; N 8.0%. Found: C 71.5; H 6.8; N 8.0.

11.

1-L-α-Phenylethyl-4-methyl-4-(3′,4′-dimethoxybenzyl)-2-imidazolin-5-one

In a experiment similar to that described in Example C. 10., 1-L-α-phenylethyl-4-methyl-2-imidazolin-5-one is employed instead of α-isocyanopropionic acid L-α-phenylethylamide. The diastereomer mixture obtained shows the same composition (ratio 80:20=60% asymmetric induction).

12.

1-L-α-Phenylethyl-4-methyl-4-(3′,4′-dimethoxybenzyl)-2-imidazolin-5-one

In an experiment similar to that described in Example C. 10., 3,4-dimethoxybenzyl bromide is employed instead of 3,4-dimethoxybenzyl chloride. Analysis of the NMR spectrum (220 MHz, $CDCl_3$) shows that the diastereomer ratio in the imidazolinone obtained is 90:10 (asymmetric induction 80%).

13.

1-L-α-Phenylethyl-4-methyl-4-(3',4'-dimethoxybenzyl)-2-imidazolin-5-one 1.3 g (11 mmoles) of potassium tert.-butanolate are added to a solution of 2.05 g (10 mmoles) of α-isocyanopropionic acid L-α-phenylethylamide in 20 ml of tetrahydrofuran at −25° C. The mixture is stirred for 10 minutes at 0° C., 1.9 g (10 mmoles) of 3,4-dimethoxybenzyl chloride are added and stirring is continued for one hour at 20° C.

The mixture is worked up as described in Example C. 10. and 3.6 g of 1-L-α-phenylethyl-4-methyl-4(3',4'-dimethoxybenzyl)-2-imidazolin-5-one are obtained. Analysis of the NMR spectrum (220 MHz, $CDCl_3$) shows a ratio of the diastereomers of 78:22 (assymetric induction 56%).

14.

1-L-α-Phenylethyl-4-methyl-4-(3',4'-dimethoxybenzyl)-2-imidazolin-5-one

A solution of 2.05 g (10 mmoles) of α-isocyanopropionic acid L-α-phenylethylamide and 1.9 g (10 mmoles) of 3,4-dimethoxybenzyl chloride in 10 ml of methylene chloride is added dropwise in the course of 30 minutes, at 25° C., to a vigorously stirred mixture of 20 g of 50% strength sodium hydroxide solution and 10 ml of methylene chloride, to which 100 mg of triethylbenzylammonium chloride have been added as a phase transfer catalyst. When the exothermic reaction has subsided, the mixture is heated for 3 hours at 40° C. The phases are separated. The methylene chloride phase is washed with water, dried and concentrated to dryness. 3.6 g of 1-L-α-phenylethyl-4-methyl-4-(3',4'-dimethoxybenzyl)-2-imidazolin-5-one remain; the NMR spectrum (220 MHz, $CDCl_3$) of this material shows a ratio of the diastereomers of 83:17 (asymmetric induction 66%).

Similar reaction mixtures using the cataysts shown below give the following results:

Tetrabutylammonium bromide in methylene chloride: diastereomer ratio 80:20.

Dimethyldibenzylammonium chloride in methylene chloride: diastereomer ratio 80:20.

Triethylbenzylammonium chloride in toluene: -diastereomer ratio 70:30.

15.

1-L-α-Phenylethyl-2,4-dimethyl-4(3',4'-dimethoxybenzyl)-2-imidazolin-5-one

In an experiment similar to that described in Example C. 10., 1-L-α-phenylethyl-2,4-dimethyl-2-imidazolin-5-one is employed instead of α-isocyanopropionic acid L-α-phenylethylamide. The resulting crude product, consisting of 3.7 g of 1-L-α-phenylethyl-2,4-dimethyl-4-(3',4'-dimethoxybenzyl)-2-imidazolin-5-one, contains, according to NMR analysis (220 MHz, $CDCl_3$), the diastereomers in a ratio of 71:29.

After purification by filtration over a silica gel column (methylene chloride, ethyl acetate) the diastereomer formed in the minor proportion is obtained in a crystalline form by suspension in ether; melting point 123°–124° C.

IR spectrum (KBr): 1,720 (C=O), 1,635 $cm^{-1}$ (C=N).

$C_{22}H_{26}N_2O_3$ (366): Calculated: C 72.1; H 7.1; N 7.7. Found: C 71.9; H 7.2; N 7.8.

16.

1-Lα-Phenylethyl-2,4-dimethyl-4-(3',4'-dimethoxybenzyl-2-imidazolin-5-one 1.3 g (11 mmoles) of potassium tert.-butanolate are added to a solution of 2.2 g (10 mmoles) of 1-L-α-phenylethyl-2,4-dimethyl-2-imidazolin-5-one in 20 ml of tetrahydrofuran at −25° C. The mixture is stirred for 10 minutes at 0° C., 1.9 g (10 mmoles) of 3,4-dimethoxybenzyl chloride are added and the batch is stirred for 12 hours at room temperature.

Working up is carried out as described in Example C. 10. and 3.7 g of 1-L-α-phenylethyl-2,4-dimethyl-4-(3',4'-dimethoxybenzyl)-2-imidazolin-5-one (C. 15.) are obtained. Analysis of the NMR spectrum (220 MHz, $CDCl_3$) shows a ratio of the diastereomers of 60:40 (asymmetric induction 20%).

17.

1-(−)-Nopinyl-4-methyl-4-(3',4'-dimethoxybenzyl)-2-imidazolin-5-one

In an experiment similar to that described in Example C. 9., 9.5 g (50 mmoles) of 3,4-dimethoxybenzyl chloride are employed instead of benzyl bromide. The resulting oily product, consisting of 19.2 g of 1-(−)-nopinyl-4-methyl-4-(3',4'-dimethoxybenzyl)-2-imidazolin-5-one, contains, according to NMR analysis (220 MHz, $CDCl_3$), the diastereomers in a ratio of 69:31 (asymmetric induction 38%). Purification is effected by filtration over silica gel (methylene chloride; ethyl acetate).

IR spectrum (film): 1,720 (C=O), 1,600 $cm^{-1}$ (C=N).

$C_{22}H_{30}N_2O_3$ (370): Calculated: N 7.6. Found: N 7.5.

18.

1-L-α-Phenylethyl-4-methyl-4-p-methoxy-benzyl-2-imidazolin-5-one 1.3 g (11 mmoles) of potassium tert.-butanolate are added to a solution of 2.0 g (10 mmoles) of isocyanopropionic acid L-α-phenylethylamide in 20 ml of tetrahydrofuran at −25° C. The mixture is stirred for 10 minutes at 0° C. and is cooled to −65° C., and 1.6 g (10 mmoles) of p-methoxybenzyl chloride are added at this temperature. When the mixture has returned to room temperature, it is worked up as described in Example C. 10. 3.3 g of crude 1L-α-phenylethyl-4-methyl-4-p-methoxybenzyl-2-imidazolin-5-one are isolated. According to NMR analysis (220 MHz, $CDCl_3$), this product contains the diastereomers in a ratio of 86:14 (asymmetric induction 72%).

In order to isolate the diastereomer formed in excess, the crude product is extracted with cyclohexane, the solvent is distilled from the extract and the residue is recrystallized from ether; melting point 72°–73° C.

IR spectrum (KBr): 1,710 (C=O), 1,610 $cm^{-1}$ (C=N).

$C_{20}H_{22}N_2O_2$ (322): Calculated: N 8.7. Found: N 8.7.

19.

1-L-α-Phenylethyl-2,4-dimethyl-4-p-methoxybenzyl-2-imidazolin-5-one 1.3 g (11 mmoles) of potassium tert.-butanolate are added to a solution of 2.2 g (10 mmoles) of 1-L-α-phenylethyl-2,4-dimethyl-2-imidazolin-5-one in 20 ml of tetrahydrofuran at −25° C. The mixture is stirred for 10 minutes at 0° C. and is then cooled to −65° C., and at this temperature 1.6 g (10 mmoles) of p-methoxybenzyl chloride are added. When the mixture has returned to room temperature, it is worked up as described in C. 10. 3.3 g of crude 1-L-α-phenylethyl-2,4-dimethyl-4-p-methoxybenzyl-2-imidazolin-5-one are isolated. Analysis of the NMR spectrum (220 MHz, $CDCl_3$) shows a ratio of the diastereomers of 64:36 (asymmetric induction 28%). Purification is carried out by filtration over silica gel (methylene chloride, ethyl acetate).

IR spectrum (film): 1,725 (C═O), 1,635 $cm^{-1}$ (C═N).

$C_{21}H_{24}N_2O_2$ (336): Calculated: C 75.0; H 7.2; N 8.3. Found: C 74.5; H 7.2; N 8.2.

20.

1-L-α-Phenylethyl-4-methyl-4-p-nitrobenzyl-2-imidazolin-5-one

In an experiment similar to that described in Example C. 18., 1.7 g (10 mmoles) of p-nitrobenzyl chloride are employed instead of methoxybenzyl chloride. 3.3 g of crystalline 1-L-α-phenylethyl-4-p-nitrobenzyl-2-imidazolin-5-one are isolated; according to the NMR spectrum (220 MHz, $CDCl_3$), this product contains the diastereomers in the ratio of 70:30 (asymmetric induction 40%). Purification is effected by recrystallization from ethyl acetate; melting point 138°-139° C.

IR spectrum (KBr): 1,710 (C═O), 1,600 $cm^{-1}$ (C═N).

$C_{19}H_{19}N_3O_3$ (337): Calculated: C 67.6; H 5.7; N 12.5. Found: C 67.5; H 5.6; N 12.4.

21.

1-L-α-Phenylethyl-2,4-dimethyl-4-p-nitrobenzyl-2-imidazolin-5-one

In an experiment similar to that described in C. 19., 1.7 g (10 mmoles) of p-nitrobenzyl chloride are employed instead of p-methoxybenzyl chloride. 3.3 g of oily 1-α-phenylethyl-2,4-dimethyl-4-p-nitrobenzyl-2-imidazolin-5-one are isolated; according to the NMR spectrum (220 MHz, $CDCl_3$), this product contains the diastereomers in the ratio of 62:38 (asymmetric induction 24%). Purification is effected by filtration over silica gel (methylene chloride, ethyl acetate).

IR spectrum (film): 1,725 (C═O), 1,630 $cm^{-1}$ (C═N).

$C_{20}H_{21}N_3O_3$ (351): Calculated: C 68.3; H 6.0; N 11.9. Found: C 68.1; H 6.1; N 11.8.

22.

1-L-α-Phenyl-ethyl-2,4-dimethyl-4-o-chlorobenzyl-2-imidazolin-5-one

In an experiment similar to that described in C. 19., 1.6 g (10 mmoles) of o-chlorobenzyl chloride are employed instead of p-methoxybenzyl chloride. 3.5 g of oily 1-L-α-phenylethyl-2,4-dimethyl-4-o-chlorobenzyl-2-imidazolin-5-one are isolated; according to the NMR spectrum (220 MHz, $CDCl_3$), this product contains the diastereomers in the ratio of 70:30 (asymmetric induction 40%).

The diastereomers are separated by column chromatography over silica gel (methylene chloride, ethyl acetate). The diastereomer formed in excess is characterized as follows:

Melting point 92°-93° C. (after recrystallization from petroleum ether)

IR spectrum (film): 1,720 (C═O), 1,630 $cm^{-1}$ (C═N).

$C_{20}H_{21}ClN_2O$ (340.5): Calculated: C 70.4; H 6.2; N 8.2. Found: C 70.7; H 6.3; N 8.2.

23.

1-L-α-Phenylethyl-2,4-dimethyl-4-p-chlorobenzyl-2-imidazolin-5-one

In an experiment similar to that described in Example C. 19., 1.6 g (10 mmoles) of p-chlorobenzyl chloride are employed in place of p-methoxybenzyl chloride. 3.5 g of oily 1-L-α-phenylethyl-2,4-dimethyl-4-p-chlorobenzyl-2-imidazolin-5-one are isolated; according to the NMR spectrum (220 MHz, $CDCl_3$), this product contains the diastereomers in the ratio of 72:28 (asymmetric induction 44%). Purification is effected by filtration over silica gel (methylene chloride, ethyl acetate).

IR spectrum (film): 1,725 (C═O), 1,635 $cm^{-1}$ (C═N).

$C_{20}H_{21}ClN_2O$ (340.5): Calculated: C 70.4; H 6.2; N 8.2. Found: C 70.2; H 6.4; N 8.1.

24.

1-L-α-Phenylethyl-4-methyl-4-cyanomethyl-2-imidazolin-5-one

In an experiment similar to that described in Example C. 18, 0.8 g (10 mmoles) of chloroacetonitrile is employed in place of p-methoxybenzyl chloride. 2.5 g of oily 1L-α-phenylethyl-4-methyl-4-cyanomethyl-2-imidazolin-5-one are isolated; according to the NMR spectrum (220 MHz, $CDCl_3$), this product contains the diastereomers in the ratio of 67:33 (asymmetric induction 35%). Purification is effected by filtration over silica gel (methylene chloride, ethyl acetate).

IR spectrum (film): 2,250 (C═N), 1,730 (C═O), 1,620 $cm^{-1}$ (C═N).

$C_{14}H_{15}N_3O$ (241): Calculated: N 17.4. Found: 17.3.

25.

1-L-α-Phenylethyl-2,4-dimethyl-4-cyanomethyl-2-imidazolin-5-one

In an experiment similar to that described in Example C. 19, 0.8 g (10 mmoles) of chloroacetonitrile is employed in place of p-methoxybenzyl chloride. 2.4 g of oily 1-L-α-phenylethyl-2,4-dimethyl-4-cyanomethyl-2-imidazolin-5-one are isolated; according to the NMR spectrum (220 MHz, $CDCl_3$), this product contains the diastereomers in the ratio of 62:38 (asymmetric induction 24%). Purification is effected by filtration over silica gel (methylene chloride, ethyl acetate).

IR spectrum (film): 1,730 (C═O), 1,630 $cm^{-1}$ (C═N).

$C_{15}H_{17}N_3O$ (255): Calculated: C 70.5; H 6.7; N 16.5. Found: C 70.5; H 6.9; N 16.1.

26.

1-L-α-Phenylethyl-2,4-dimethyl-4-allyl-2-imidazolin-5-one 12.5 ml of a 16.1 N solution of n-butyl-lithium (20 mmoles) in hexane are added dropwise to a solution of 4.4 g (20 mmoles) of 1-L-α-phenylethyl-2,4-dimethyl-2-imidazolin-5-one in 30 ml of tetrahydrofuran at −60° C. 2.4 g (20 mmoles) of allyl bromide are then added dropwise at the same temperature. After the mixture has returned to room temperature, it is worked up as described in Example C. 10. After distillation (boiling point 135°-140° C./0.3 mm Hg), 4.2 g of 1-L-α-phenylethyl-2,4-dimethyl-4-allyl-2-imidazolin-5-one are obtained; according to the NMR spectrum (220 MHz, $CDCl_3$) this product contains the diastereomers in the ratio of 78:22 (asymmetric induction 56%).

IR spectrum (film): 1,720 (C=O), 1,630 $cm^{-1}$ (C=N).

$C_{16}H_{20}N_2O$ (256): Calculated: C 75.0; H 7.8; N 10.9. Found: C 74.7; H 7.9; N 11.0.

27 to 40.

General procedure: 10 mmoles of the stated base (butyl-lithium at −70° C.; potassium tert.-butanolate or sodium hydride at −25° C.) are added to a solution of 2.8 g (10 mmoles) of α-isocyano-β-phenyl-propionic acid L-α-phenylethylamide in 45 ml of dry solvent. The mixture is stirred for 10 minutes at room temperature and is then cooled to −70° C., and the alkylating agent is added. When the mixture has returned to room temperature, the solvent is distilled off, the residue is taken up in 45 ml of methylene chloride and the solution is washed with twice 25 ml of water. The crude product which remains after concentrating the methylene chloride solution is purified by filtration over alumina (activity level II, ether/petroleum ether) and is characterized by the IR and NMR spectra and by elementary analysis.

The results are summarized in Table 1.

TABLE 1

$R^1$ = L-α-phenylethyl, $R^2$ = H, $R^3$ = benzyl

| Alkylating agent $R^4X$ | Base/Solvent | Yield, % | Asymmetric induction, % |
|---|---|---|---|
| 27 $CH_3I$ | $C_4H_9Li$—THF | 90 | 20 |
| 28 $CH_3I$ | KO—t-$C_4H_9$—THF | 90 | 20 |
| 29 $CH_3I$ | NaH—DMSO/ether | 90 | 11 |
| 30 $C_2H_5I$ | $C_4H_9Li$—THF | 65 | 23 |
| 31 $C_2H_5I$ | KO—t-$C_4H_9$—THF | 85 | 25 |
| 32 n-$C_4H_9I$ | $C_4H_9Li$—THF | 72 | 55 |
| 33 n-$C_4H_9I$ | KO—t-$C_4H_9$—THF | 70 | 50 |
| 34 i-$C_3H_7I$ | KO—t-$C_4H_9$—THF | 62 | 65 |
| 35 $CH_2$=CH—$CH_2I$ | $C_4H_9Li$—THF | 90 | 36 |
| 36 $CH_2$=CH—$CH_2Br$ | $C_4H_9Li$—THF | 90 | 43 |
| 37 $CH_2$=CH—$CH_2Cl$ | $C_4H_9Li$—THF | 85 | 39 |
| 38 $CH_2$=CH—$CH_2$OTos | $C_4H_9Li$—THF | 90 | 23 |
| 39 p-Br—$C_6H_4$—$CH_2Br$ | $C_4H_9Li$—THF | 90 | ≧95 |
| 40 $BrCH_2CO_2C_2H_5$ | $C_4H_9Li$—THF | 75 | 31 |

41. to 49.

Compounds of formula I from isocyanoacetic acid L-α-phenylethylamide

General procedure: 20 mmoles of n-butyl-lithium solution (13 ml of a 1.55 N solution in hexane) are added dropwise to a solution of 1.9 g (10 mmoles) of isocyanoacetic acid L-α-phenyl-ethylamide in 25 ml of dry tetrahydrofuran at −70° C. After 10 minutes, 10 mmoles of the first alkylating agent, dissolved in 10 ml of tetrahydrofuran, are added at the same temperature.

The mixture is allowed to warm up and at +10° C. the second alkylating agent, dissolved in 10 ml of tetrahydrofuran, is added. After stirring for 2 hours, the mixture is worked up as described for C. 27. The products obtained are characterized by the IR and NMR spectra and by elementary analysis.

The results are summarized in Table 2.

TABLE 2

$R^1$ = L-α-phenylethyl, $R^2$ = H

| 1st Alkylating agent $R^3X$ | 2nd Alkylating agent $R^4$ | Yield, % | Asymmetric induction, % |
|---|---|---|---|
| 41 $CH_3I$ | $C_6H_5CH_2Br$ | 90 | 95 |
| 42 $C_6H_5CH_2Br$ | $CH_3I$ | 90 | 20 |
| 43 $CH_2$=CH—$CH_2Br$ | $C_6H_5CH_2Br$ | 75 | 90 |
| 44 $C_6H_5CH_2Br$ | $CH_2$=CH—$CH_2Br$ | 69 | 45 |
| 45 p-Br—$C_6H_4$—$CH_2Br$ | $C_6H_5CH_2Br$ | 72 | 95 |
| 46 $C_2H_5I$ | $C_6H_5CH_2Br$ | 85 | 95 |
| 47 n-$C_4H_9I$ | $C_6H_5CH_2Br$ | 58 | 95 |
| 48 i-$C_3H_7I$ | $C_6H_5CH_2Br$ | 78 | 95 |
| 49 3,4-$(CH_3O)_2$—$C_6H_3CH_2Cl$ | $CH_3I$ | 60 | 20 |
| 50 n-$C_3H_7I$ | $C_6H_5CH_2Br$ | 77 | 90 |

51.

1-L-α-Carbo-tert.-butoxy-ethyl-4-benzyl-4-methyl-2-imidazolin-5-one 1.13 g of N-(α-isocyano-propionyl)-L-alanine tert.-butyl ester and 0.85 g of benzyl bromide are reacted by the method described in Example C. 1. 1.4 g (89%) of 1-L-α-carbo-tert.-butoxy-ethyl-4-benzyl-4-methyl-2-imidazolin-5-one are obtained and are purified by chromatography (with ether over alumina of activity level II). 0.7 g (45%) of pure compound of melting point 97° C. ($CH_2Cl_2$:ether:petroleum ether=1:10:10) remain. The diastereomer ratio is 6:1, corresponding to an asymmetric induction of 72%.

$^1$H-NMR (100 MHz, $CSCl_3$): τ=9.12 (d, $CH_3$, J=8 Hz), 8.62 (s, tert.-butyl), 8.56 (s, 4—$CH_3$), 5.64 (q, C—H, J=8 Hz), 2.86 (s, phenyl), for the LL diastereomer: 6.96 (s, $CH_2$), 2.42 (s, 2—CH), for the DL diastereomer: 6.99 (s, $CH_2$), 2.38 (s, 2—CH).

IR (KBr): ν=1,615 (N=C), 1,735 $cm^{-1}$ (C=O).

52.

1-L-α-Carbo-tert.-butoxy-ethyl-4-allyl-4-methyl-2-imidazolin-5-one 1.13 g of N-(α-isocyano-propionyl)-L-alanine tert.-butyl ester and 0.6 g of allyl bromide are reacted by the method described in Example 50. 1.1 g (85%) of 1-L-α-carbo-tert.-butoxy-ethyl-4-allyl-4-methyl-2-imidazolin-5-one are obtained. Distillation gives 1.0 g (75%) of pure compound of boiling point 95°-100° C./0.01 mm Hg. The diastereomer ratio is 2:1, corresponding to an asymmetric induction of 33%.

$^1$H-NMR (100 MHz, $CDCl_3$): τ=8.56 (s, tert.-butyl), 7.53 (d, $CH_2$, J=7 Hz), 2.18 (s, 2—CH).

IR (film): ν=1,615 (N=C), 1,725 $cm^{-1}$ (C=O).

(Separation by adding the paramagnetic reagent $Eu(tfc)_3$.).

53.

1-L-α-Phenylethyl-4-isobutyl-4-benzyl-2-imidazolin-5-one 1.3 g (11 mmoles) of 95% strength potassium tert.-butanolate are introduced into a solution of 2.5 g (10 mmoles) of 1-L-α-phenylethyl-4-isobutyl-2-imidazolin-5-one in 20 ml of THF at −30° C. The mixture is stirred for 10 minutes at 0° C. and is then cooled to −65° C., and a solution of 1.75 g (10 mmoles) of benzyl bromide is added dropwise. The batch is worked up as described in Example B. 1. and the product is purified by filtration over silica gel (methylene chloride, ethyl acetate). 1.1 g of 1-L-α-phenylethyl-4-isobutyl-4-benzyl-2-imidazolin-5-one are obtained, melting point 116° C.

Analysis of the NMR spectrum (220 MHz, $CDCl_3$) shows that the product contains at least 95% of pure diastereomer.

Melting point (after recrystallization from isopropanol) 128° C.

IR spectrum (KBr): 1,700 (C=O), 1,600 $cm^{-1}$ (C=N).

$C_{22}H_{26}N_2O$ (334): Calculated: C 79.0; H 7.8; N 8.4. Found: C 79.1; H 7.6; N 8.4.

54.

1-L-α-Phenylethyl-4-methyl-4-(3',4'-methylenedioxybenzyl)-2-imidazolin-5-one 4.05 g (20 mmoles) of α-isocyanopropionic acid L-α-phenylethylamide, 3.4 g (20 mmoles) of 3,4-methylenedioxybenzyl chloride and 200 mg of triethylbenzylammonium chloride are dissolved in 40 ml of methylene chloride. After adding 3.2 ml of water, the mixture is heated to the boil. 3.2 g of 50% strength sodium hydroxide solution (40 mmoles) are added dropwise, with vigorous stirring, in the course of 15 minutes, stirring is continued for 30 minutes, the mixture is cooled and the phases are separated. The methylene chloride phase is washed with water and concentrated to dryness. 3.8 g of oily 1-L-α-phenylethyl-4-methyl-4-(3',4'-methylenedioxybenzyl)-2-imidazolin-5-one remain; the NMR spectrum (220 MHz, $CDCl_3$) of this product indicates a ratio of the diastereomers of 70:30 (asymmetric induction 40%).

The product is obtained in a pure form by filtration over silica gel (methylene chloride, ethyl acetate).

IR spectrum (film): 1,710 (C=O), 1,600 $cm^{-1}$ (C=N).

$C_{20}H_{20}N_2O_3$ (336): Calculated: C 71.5%; H 5.9%; N 8.3%. Found: C 71.4%; H 5.9%; N 8.4%.

D. HYDROLYSIS TO THE OPTICALLY ACTIVE AMINOACIDS

1. L-α-Methylphenylalanine

A solution of 4.2 g of crude 1-L-α-phenylethyl-4-methyl-4-benzyl-2-imidazolin-5-one obtained as described in Example C. 1., in 20 ml of methanol and 5 ml of water, is saturated with hydrogen chloride gas and boiled for 24 hours under reflux. The solvent is distilled off, the residue is taken up in 20 ml of half-concentrated hydrochloric acid and the solution is boiled under reflux for 24 hours. It is then allowed to cool and is extracted with twice 20 ml of methylene chloride, and the extract is concentrated to dryness. The residue is dissolved in a little absolute ethanol and propylene oxide is added. Hereupon 1.8 g of L-α-methylphenylalanine precipitate, and are filtered off and dried (67% yield).

Melting point 290° C., with decomposition (the literature gives a melting point of 316° C.).

$[\alpha]_D^{20} = -4.7°$ (C=1.025 in 1 N HCl)

The literature gives $[\alpha]_D^{20} = -4.5°$ (C=1 in 1 N HCl)

Hydrochloride:

Melting point 249° C., with decomposition.

$[\alpha]_D^{20} = 8.55°$ (C=1.03 in $H_2O$)

The literature gives $[\alpha]_D^{20} = -8.6°$ (C=1 in $H_2O$).

Comparison of the measured values with the data from the literature shows that the α-methylphenylalanine obtained is optically pure and hence also confirms the result of the NMR analysis, namely that at the intermediate stage the imidazolinone contains at least 95% of pure diastereomer.

The literature data are given in the article by K. Weinges et al., Chem. Ber. 104 (1971), 3594.

2. L-(−)-N-Acetyl-α-methyl-β-(3,4-dimethoxyphenyl)-alanine 7.0 g of the diastereomer mixture of 1-L-α-phenylethyl-4-methyl-4-(3',4'-dimethoxybenzyl)-2-imidazolin-5-one obtained as described in Example C. 10., are hydrolyzed to the aminoacid by heating with aqueous-ethanolic potassium hydroxide (6 g in 40 ml of ethanol and 20 ml of water). After distilling off the solvent, the residue is taken up in water. The aqueous phase is extracted with methylene chloride and is concentrated under reduced pressure. The dry residue is heated in dimethylformamide, in the presence of 6 g of acetic anhydride, for one hour at 90°. Undissolved salt is filtered off, the filtrate is concentrated under reduced pressure and the residue is taken up in 50 ml of water. The solution is acidified to pH 1 with hydrochloric acid. The precipitate of N-acetyl-α-methyl-β-(3,4-dimethoxyphenyl)-alanine, which crystallizes on rubbing is filtered off, washed with a little cold water and dried. Melting point 189°-191° C.; $[\alpha]_D^{27°} = -28.8°$ (C=2; $CH_3OH$).

The conversion of the imidazolinone into the N-acetylaminoacid, described above, is advantageous because the product has a relatively high optical rotation, so that the asymmetric induction can be determined accurately.

The literature gives the following values for the pure enantiomer: Tristram et al., J. Org. Chem. 29 (1964), 2053: melting point 192°-194° C., $[\alpha]_D^{25} = -55°$ (C=1, $CH_3OH$); Slater et al., J. Org. Chem. 29 (1964), 1424: melting point 186°-187° C., $[\alpha]_D = -21°$ (acetone).

The N-acetyl compound obtained from optically pure L-(+)-N-formyl-α-methyl-β-(3,4-dimethoxyphenyl)-alanine (cf. German Laid-Open Application DOS No. 2,406,898) by hydrolysis and subsequent acetylation gives the following values after recrystallization from acetone: melting point 186°-187° C., $[\alpha]_D^{27} = -52°$ (C=2, $CH_3OH$). From this, the asymmetric induction is calculated to be 55%, in good agreement with the result of 60% obtained by NMR analysis of the diastereomer mixture at the imidazolinone stage.

3. L-α-Methyl-DOPA

A solution of 14.1 g (40 mmoles) of the diastereomer mixture of 1-L-α-phenylethyl-4-methyl-4-(3',4'-dimethoxybenzyl)-2-imidazolin-5-one, obtained as described in Example C. 14., in aqueous-ethanolic potassium hydroxide (18 g in 80 ml of ethanol and 40 ml of water) is refluxed for 20 hours. After distilling off the ethanol and adding water, the aqueous phase is extracted with methylene chloride. The methylene chloride solution contains the L-α-phenylethylamine formed on hydrolysis, and some residual α-methyl-β-(3,4-dimethoxyphenyl)-alanine L-α-phenylethylamide, the primary product of the hydrolytic ring scission of the imidazolinone employed. The aqueous phase is brought to pH 6-6.5 by adding hydrochloric acid. The precipitate is filtered off and dried in a high vacuum at 80° C. 7.7 g of α-methyl-β-(3,4-dimethoxyphenyl)-alanine are obtained as the enantiomer mixture, melting point 244°-246° C.

7.2 g (30 mmoles) of this enantiomer mixture are refluxed with 60 ml of 48% strength hydrobromic acid for 12 hours. The hydrobromic acid is then distilled off under reduced pressure at 70° C. The residue is digested in 10 ml of water, the water is distilled off, the residue now obtained is taken up in 20 ml of water, a little sodium pyrosulfite and active charcoal are added and the solution is filtered, The filtrate is brought to pH 6.3 by adding about 3 ml of concentrated ammonia solution. The precipitate is filtered off, rinsed with a little water and with acetone and dried at 60° C. under 3 mm Hg. 4.2 g of L-α-methyl-DOPA (containing about 11% of water as determined by the Karl Fischer method) are obtained, melting point 289°-291° C., $[\alpha]_D^{20}=-4.7°$ (C=2 in 0.1 N HCl).

In the same way, 8.1 g of optically pure L-α-methyl-β(3,4-dimethoxyphenyl)-alanine, melting point 259° C. (after recrystallization from water), are obtained from pure imidazolinone diastereomer prepared as described in Example C 10.

7.2 g of this aminoacid give 6.1 g of L-α-methyl-DOPA, having the stated properties.

4. L-α-Methyl-DOPA

1-L-α-Phenylethyl-4-methyl-4-(3',4'-methylenedioxybenzyl)-2-imidazolin-5-one, obtained as described in Example C. 54., is hydrolyzed as described in D. 3. to give α-methyl-β-(3,4-methylenedioxyphenyl)-alanine.

$C_{11}H_{15}NO_3$ (209): Calculated: C 63.2; H 7.2. Found: C 63.0; H 7.3.

NMR spectrum (60 MHz, $D_2O$): δ=1.47 (s); 2.8 and 3.2 (AB, J=15 Hz); 3.7 (s); 6.95 ppm (AA'BB', $J_{AB}=8.6$ Hz).

The optical rotations confirm the asymmetric induction determined by NMR spectroscopy in Example C. 18.

The hydrolysis to L-α-methyl-tyrosine can be carried out with hydrobromic acid under the conditions described in D. 3.

Table 3 gives further examples of the hydrolysis of formula I compounds to form optically active amino acids. $R^1$ always denotes L-α-phenylethyl and the amino acids are characterized as N-acetyl derivatives. The 2-imidazolin-5-ones a to e are prepared from 1-L-α-phenylethyl-4-methyl-2-imidazolin-5-one by reaction in tetrahydrofuran in the presence of one equivalent of butyllithium as the base with a bromide corresponding to the radical $R^4$ indicated. Compounds f to i are prepared from isocyanoacetic acid L-α-phenylethylamide by reaction in tetrahydrofuran in the presence of 2 equivalents of butyllithium, initially with $R^3$ iodide and then with benzyl bromide.

TABLE 3

| | 2-Imidazolin-5-one | | Yield, | Asymmetric induction, | N-Acetylamino-acid | | m.p. |
|---|---|---|---|---|---|---|---|
| | $R^3$ | $R^4$ | % | % | $[\alpha]_D^{21}$ | (C, Solvent) | °C. |
| a | $CH_3$ | [Naphth-1-yl]methyl | 84 | >95 | −91.38° | (1.08, $CH_3OH$) | 222 |
| b | $CH_3$ | [Naphth-2-yl]methyl | 87 | >95 | −92.31° | (1.62, $CH_3OH$) | 212 |
| c | $CH_3$ | [Thien-2-yl]methyl | 80 | >95 | −37.5° | (1.0, $CH_3OH$) | 224 |
| d | $CH_3$ | [Benzothien-3-yl]methyl | 87 | >95 | −69.5° | (1.0, DMF) | 244 |
| e | $CH_3$ | [2-Bromo-benzofuran-3-yl]methyl | 88 | >95 | −77.6° | (1.0, $CH_3OH$) | 239 |
| f | $C_2H_5$ | $CH_2—C_6H_5$ | 85 | ~95 | +1.901° | (1.875,$CH_3OH$) | 223-225 |
| g | $CH_2—CH=CH_2$ | $CH_2—C_6H_5$ | 75 | ~90 | +2.18° | (1.665,$CH_3OH$) | 264-265 |
| h | n-$C_3H_7$ | $CH_2—C_6H_5$ | 77 | ~90 | +1.29° | (1.419,$CH_3OH$) | 238-240 |
| i | $C_4H_9$ | $CH_2—C_6H_5$ | 67 | ~95 | +0.849° | (1.46, $CH_3OH$) | 199-200 |

The asymmetric induction calculated from the optical rotation of the hydrochloride, $[\alpha]_D^{25}=+3.0°$ (C=1, $CH_3OH$) in comparison with the optical rotation of the optically pure compound, $[\alpha]_D^{20}=+8.1°$ (C=1, $CH_3OH$) is 37%, in good agreement with the value obtained in Example C. 54. (Suzuki et al., Chem. and Ind., 1972, 687).

The hydrolysis to give α-methyl-DOPA is carried out in accordance with conventional methods, for example with 20% strength hydrochloric acid in the presence of phenol, as described in German Published Application DAS No. 2,302,937 (Example 1.5).

5. L-α-Methyl-β-methoxyphenyl-alanine

A mixture of 6.45 g (20 mmoles) of 1-L-α-phenylethyl-4-p-methoxyphenyl-4-methyl-2-imidazolin-5-one and 5.4 g (80 mmoles) of 85% strength potassium hydroxide in 20 ml of ethylene glycol is heated for 5 hours at 150° C. Ethylene glycol, and L-α-phenylethylamine formed, are distilled off under reduced pressure on a rotary evaporator. The residue is partitioned between water and methylene chloride. The aqueous phase is neutralized with dilute hydrochloric acid and concentrated by evaporation under reduced pressure. Extraction of the residue with ethanol gives 4.2 g of crude α-methyl-β-p-methoxyphenyl-alanine, melting point 243°-244° C., $[\alpha]_D^{25}=-3.1°$ (C=1, 1 N HCl).

Recrystallization from water gives the optically pure aminoacid, melting point 265°-266° C. $[\alpha]_D^{25}=-4.4°$ (C=1, 1 N HCl).

We claim:

1. A 2-imidazolin-5-one of the formula I

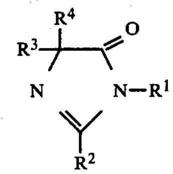

where $R^1$ is L-α-phenylethyl, (+)-3-pinyl-methyl, (−)-nopinyl or L-α-carbo-tert.-butoxyethyl, $R^2$ is hydrogen, alkyl of 1 to 4 carbon atoms, benzyl or phenyl, $R^3$ and $R^4$ are different, and $R^3$ is alkyl of 1 to 4 carbon atoms;

alkyl of 1 to 4 carbon atoms substituted by alkoxy of 1 to 4 carbon atoms, by alkylthio of 1 to 4 carbon atoms, by dialkylamino, each alkyl of which contains 1 to 4 carbon atoms, by benzyloxy, by benzylthio, by acyloxy where the acyl radical contains 1 to 4 carbon atoms, by cyano, by carbalkoxy where the alkyl contains 1 to 4 carbon atoms, by benzoyl, by bromo-benzoyl, by benzyl or by phenyl;

benzyl, benzyl which is mono- or di-substituted by alkoxy of 1 to 4 carbon atoms, by acyloxy where the acyl radical contains from 1 to 4 carbon atoms, by benzyloxy, by methylenedioxy, or by alkyl of 1 to 4 carbon atoms; or phenyl;

$R^4$ is alkyl of 1 to 6 carbon atoms;

alkyl of 1 to 6 carbon atoms substituted by alkoxy of 1 to 4 carbon atoms, by alkylthio of 1 to 4 carbon atoms, by benzyloxy, by cyano, by carbalkoxy where the alkyl contains from 1 to 4 carbon atoms, by benzoyl, or by benzoyl substituted by halogen;

benzyl;

benzyl which is mono- or di-substituted by alkyl of 1 to 4 carbon atoms, by alkoxy of 1 to 4 carbon atoms, by acyloxy of 1 to 4 carbon atoms, by nitro, by chloro, by bromo, by haloacetoxy, by methoxyacetoxy, by benzyloxy, or by methylenedioxy; or allyl.

2. A compound of the formula I as set forth in claim 1, where $R^1$ is L-α-phenylethyl, $R^2$ is hydrogen, $R^3$ and $R^4$ are different from one another and are methyl or benzyl, the phenyl ring being unsubstituted or monosubstituted or disubstituted by alkoxy or acyloxy (in each case of 1 to 4 carbon atoms) or benzyloxy or monosubstituted by methylenedioxy.

3. 1-L-α-phenylethyl-4-methyl-4-(3',4'-dimethoxybenzyl-2-imidazoline-5-one.

4. 1-L-α-phenylethyl-4-methyl-4-benzyl-2-imidazolin-5-one.

* * * * *